(12) United States Patent
Li et al.

(10) Patent No.: US 8,778,325 B2
(45) Date of Patent: Jul. 15, 2014

(54) WATER-SOLUBLE AND BIODEGRADABLE ANTIMICROBIAL AGENT

(75) Inventors: Chun-Yi Li, Zhongli (TW); Ken-Yuan Chang, Zhongli (TW); Chia-Chang Liu, Zhongli (TW); Ying-Nan Tsai, Zhongli (TW)

(73) Assignee: Far Eastern New Century Corporation, Taipei (TW)

( * ) Notice: Subject to any disclaimer, the term of this patent is extended or adjusted under 35 U.S.C. 154(b) by 557 days.

(21) Appl. No.: 13/098,788

(22) Filed: May 2, 2011

(65) Prior Publication Data

US 2012/0082638 A1    Apr. 5, 2012

(30) Foreign Application Priority Data

Oct. 4, 2010 (TW) .............................. 99133716 A

(51) Int. Cl.
*A61K 31/74* (2006.01)
*A61K 47/48* (2006.01)
*A01N 37/46* (2006.01)
*C08G 69/10* (2006.01)

(52) U.S. Cl.
CPC ............... *C08G 69/10* (2013.01); *A01N 37/46* (2013.01)
USPC ...................................................... 424/78.17

(58) Field of Classification Search
None
See application file for complete search history.

(56) References Cited

U.S. PATENT DOCUMENTS

| | | | |
|---|---|---|---|
| 5,126,057 A | 6/1992 | Worley et al. | |
| 5,536,813 A | 7/1996 | Charpenel et al. | |
| 5,882,357 A * | 3/1999 | Sun et al. | 8/189 |
| 5,902,818 A | 5/1999 | Worley et al. | |
| 7,335,373 B2 | 2/2008 | Worley et al. | |
| 2003/0220467 A9 | 11/2003 | McDonald et al. | |
| 2005/0014670 A1 | 1/2005 | Hodge et al. | |
| 2010/0215957 A1* | 8/2010 | Tajima | 428/401 |

FOREIGN PATENT DOCUMENTS

| | | |
|---|---|---|
| CN | 1312776 A | 9/2001 |
| TW | 200640445 A | 12/2006 |

OTHER PUBLICATIONS

English translation of abstract of CN 1312776 A (published Sep. 12, 2001).
Cheng et al. "Development of Biodegradable Polyglutamic Acid" Journal of Beijing Union University (Natural Sciences), vol. 22, No. 2, pp. 45-49, Jun. 2008.
Huang et al. "Study on Biodegradability of Copolymer of Aspartic Acid and Glutamic Acid" Journal of Harbin Institute of Technology, vol. 39, No. 8, pp. 1230-1232, Aug. 2007.
English translation of abstract of TW 200640445 A (published Dec. 1, 2006).

* cited by examiner

*Primary Examiner* — Paul Dickinson
(74) *Attorney, Agent, or Firm* — McClure, Qualey & Rodack, LLP

(57) ABSTRACT

A water-soluble and biodegradable antimicrobial agent is provided, comprising a polymer composed of a segment A and a segment B, in which, the segment A has the following formula I:

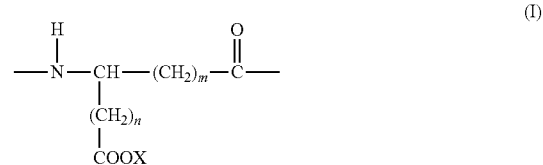

the segment B has the following formula II:

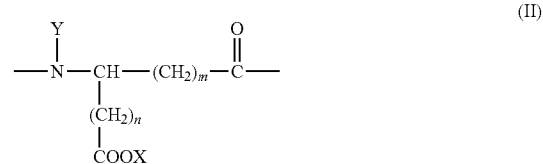

wherein the segment A and the segment B in the polymer have a molar ratio of 1:0.007-1.2, and n is 0 or 1, m is an integer of 0-2, m+n≠0, X is H, Na, K, $NH_4$, ½Ca, or ½Mg, and Y is Cl, Br, or I.

20 Claims, No Drawings

WATER-SOLUBLE AND BIODEGRADABLE ANTIMICROBIAL AGENT

RELATED APPLICATIONS

This application claims priority to Taiwan Application Serial Number 099133716, filed Oct. 4, 2010, which is herein incorporated by reference.

BACKGROUND

1. Field of Invention

The present invention relates to an antimicrobial agent, and more to particularly, to a water-soluble and biodegradable antimicrobial agent having a backbone composed of at least one repeating unit comprising N-halamine groups.

2. Description of Related Art

In our living environments, even on the human body, the presence of at least thousands of microorganisms can be found. Among the microorganisms, some are beneficial to humans and some are harmful. Beneficial microorganisms can be used to produce desired foods or chemicals, and harmful microorganisms may destroy foods or drugs in processing, storage and transportation, or in use by consumers, or even cause an infection of tissues in body. Thus, in order to avoid the potential harms by such microorganisms to humans, there exists the need for antimicrobial agents in our environment and various applications. It is currently known that many antimicrobial agents have been developed and widely used in various living applications.

Among currently developed antimicrobial agents of various types, there is a class of antimicrobial agent containing N-halamine compound as a component, which has excellent antimicrobial efficacy for bacteria, molds and viruses and the like. It is known that a N-halamine compound refers to a compound containing a halamine functional group of N—X (X may be Cl, Br, or I), which can be obtained by oxidizing a compound containing a functional group, such as amine, amide, or imide group, with an oxidant (for example, hypohalites). The N—X functional group in this type of compounds can slowly dissociate by the action of water molecules in water in the presence of microorganisms, to release oxidizing halogen ions, while the N—X functional group in this compound is reduced to an N—H functional group. The released oxidizing halogen ions can kill microorganisms such as bacteria and molds. After the N-halamine compound dissociates into the halogen ion to kill the microorganisms, it usually can be treated with the hypohalites again, so that the N—H functional group thereof can be oxidized into the N—X functional group again, thereby causing the regeneration of the sterilization function. It is known that the N-halamine compound is very useful for disinfection in family, commercial and medical places, due to having the advantages such as fast sterilization speed, high sterilization efficiency, long duration, good stability, and regeneratability of antimicrobial capability.

The research by Worley is the most representative of all the development of known antimicrobial N-halamine compounds. The research group leaded by Worley has developed many kinds of N-halamine compounds having antimicrobial property. However, all of these compounds are based on a cyclic N-halamine compound, and the structures disclosed are, for example, oxazolidinones (U.S. Pat. No. 5,902,818), imidazolidinones (U.S. Pat. No. 5,126,057), hydantoins, and spirocyclic amines, and the like. All of these structures are treated with hypochlorites to yield the N—Cl functional groups, thereby having the antimicrobial efficacy; however, whether for these monomers or the polymer, the problem of less solubility in water exists, such that its application fields, even antimicrobial property, are limited.

On the other hand, based on the protection of the environment, antimicrobial agent systems nowadays mostly tend to use an aqueous system instead of an organic solvent, thereby reducing the harms by the organic solvent to the environment. In order to be applicable in the aqueous system, Worley et al considered that a hydrophilic group can be attached onto a side chain of the polymer to obtain an antimicrobial substance having high water solubility. A quaternary ammonium salt is generally used as the hydrophilic group, thereby improving is the solubility in water. For example, Worley et al has developed an antimicrobial polymer in which siloxane is used as the skeleton and a cyclic N-halamine compound hydantoin and quaternary ammonium salt structures are attached thereon, respectively (U.S. Pat. No. 7,335,373). Therein, both siloxane and hydantoin have very poor solubility in water, and the water solubility of the antimicrobial polymer is improved mainly by the quaternary ammonium salt, which has no antimicrobial efficacy, and therefore, a longer contact time is required for such an antimicrobial agent to achieve the sufficient antimicrobial effect. Although Worley et al has designed this antimicrobial polymer structure by improving the water solubility of the cyclic N-halamine compound, the problem that it is not totally soluble in water still exists, and a small amount of alcohols still needs to be added to help to dissolve the antimicrobial polymer for using the cyclic N-halamine compound. However, this cannot completely resolve the doubts about the likely harms caused by the organic solvent to the environment. On the other hand, the structure of this antimicrobial polymer is obtained by the chemical synthesis, and during and after the synthesis, organic solvents may be used more or less and unnecessary side-products may be generated, thus, the harms caused to the environment may also occur in the manufacturing process to some extent. Furthermore, a special synthesis via multiple preparation processes is needed for such an antimicrobial polymer, which would thus be expensive. This can be confirmed by the fact that techniques for preparing such compound had been disclosed by Worley et al many years before, but up to now, no numerous products have been marketed.

Therefore, it is necessary to develop a water-soluble antimicrobial substance having biocompatibility, non-toxicity, regenerative antimicrobial capability, easy preparation, and low cost.

SUMMARY

A primary aspect of the present invention is to provide an antimicrobial agent having high water solubility and biodegradability.

In order to achieve the aspect above, the present invention provides an antimicrobial agent having high water solubility and biodegradability. The antimicrobial agent comprises a biodegradable polymer composed of a segment A and a segment B, wherein the segment A has the following formula I:

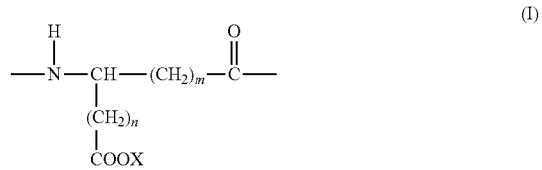

and the segment B has the following formula II:

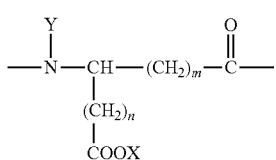
(II)

wherein the molar ratio of the segment A and the segment B in the polymer is 1:0.007-1.2, and n is 0 or 1, m is an integer of 0-2, m+n≠0, X is H, Na, K, $NH_4$, ½Ca, or ½Mg, and Y is Cl, Br, or I.

In addition to good solubility in water, the antimicrobial agent according to the present invention has the advantages such as non-toxicity, no harm to the environment, high sterilization efficiency, long duration, and regeneration of antimicrobial property.

Therefore, by using the antimicrobial agent according to the present invention, the problems of that an aqueous system cannot be used alone as solvent for synthesizing known antimicrobial agents containing a cyclic N-halamine compound and that the harm to the environment is easily caused due to its non-biodegradability can be well solved.

These and other features, aspects, and advantages of the present invention will become better understood with reference to the following description and appended claims.

It is to be understood that both the foregoing general description and the following detailed description are by examples, and are intended to provide further explanation of the invention as claimed.

DETAILED DESCRIPTION

The present invention provides an antimicrobial agent having high water solubility and biodegradability, which comprises a biodegradable polymer composed of a segment A and a segment B. The biodegradable polymer is endowed with antimicrobial property due to containing the segment B having antimicrobial property.

The segment A in the biodegradable polymer of the present invention preferably has the following formula I:

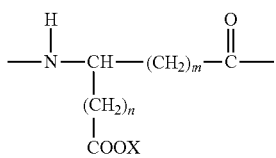
(I)

the segment B preferably has the following formula II:

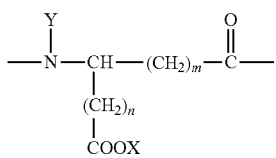
(II)

and the molar ratio of the segment A and the segment B is 1:0.007-1.2. In the formulas I and II, n is 0 or 1; m is an integer of 0-2, and m+n≠0; X is H, Na, K, $NH_4$, ½Ca, or ½Mg; and Y is Cl, Br, or I.

Preferred specific examples of the segment A in the biodegradable polymer of the present invention have the following formulas:

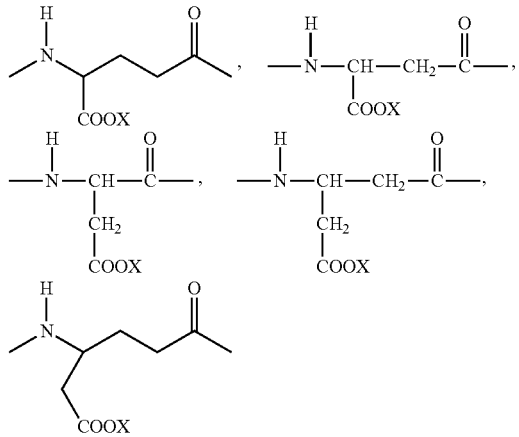

in which, X is H, Na, K, $NH_4$, ½Ca, or ½Mg.

Preferred specific examples of the segment B in the biodegradable polymer of the present invention have essentially the same formulas as those of the segment A, except for Y substituent.

The segment A and the segment B constituting the biodegradable polymer of the present invention can be composed of a single kind of segment or two or more kinds of segments in combination, respectively, which is not particularly limited herein.

A more preferred specific example of the segment A useful in the present invention is shown below:

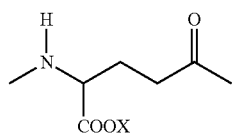

Another more preferred specific example of the segment A useful in the present invention is selected from the group consisting of a segment C and a segment D, in which the segment C has the following formula:

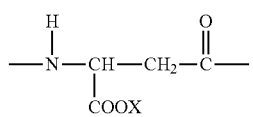

the segment D has the following formula:

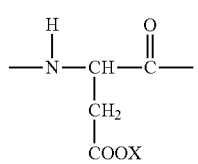

in which, X is H, Na, K, $NH_4$, ½Ca, or ½Mg.

In addition, a more preferred specific example of the segment B useful in the present invention is shown below:

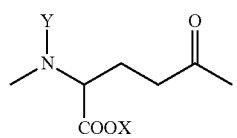

In addition, another more preferred specific example of the segment B useful in the present invention is selected from the group consisting of a segment E and a segment F, in which the segment E has the following formula:

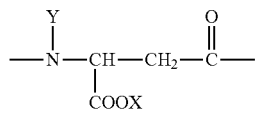

the segment F has the following formula:

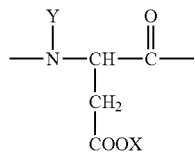

in which, X is H, Na, K, $NH_4$, ½Ca, or ½Mg; Y is Cl, Br, or I.

The ratio between the total moles of the segment C and the segment E and the total moles of the segment D and the segment F is not less than 1. (i.e. $(C+E)/(D+F)\geq 1$)

The biodegradable polymer described in the present invention is formed by polymerizing the segment A and the segment B. Thus, it may have regularity, partial regularity, no regularity, or a combination thereof. Specifically, in the biodegradable polymer of the present invention, the segment A and the segment B can be arranged in a regular manner, for example, including, but not limited to, ABABABAB, AABBAABB, AAABBAAABB .... In a partially regular manner, for example, including, but not limited to, ABABAAA-BABB, AABBAABBABABABB .... In a non-regular manner, for example, including, but not limited to, AABABB-BAA, ABBBABABBA ... etc. However, it is noted that the structure arranged in any general formula does not affect the antimicrobial function.

The biodegradable polymer of the present invention having the antimicrobial function can be prepared by any known means, which is not particularly limited herein. For example, it can be synthetically formed by directly polymerizing the segment A and the segment B. Alternately, it can be obtained from a polymer formed by only the segment A by halogenation with a halogenating agent. In this case, the polymer formed by only the segment A can be made directly from the segment A via polymerization, produced by a microorganism, isolated from a natural substance, or synthesized by a known peptide synthesizer.

The treatment of the halogenation with the halogenating agent is not particularly limited herein, for example, including soaking or spraying, where the amine linkage in the segment A is partially oxidized with the halogenating agent, thereby forming a biodegradable polymer having the antimicrobial function.

The halogenating agent useful in the present invention includes, but not limited to, perhalic acid, perhalates, halic acid, halates, halous acid, halites, hypohalous acid, hypohalites, halogen gases, trichloroisocyanuric acid (TCCA), or a combination thereof.

A preferred specific example of the halogenating agent useful in the present invention includes, but is not limited to, sodium hypochlorite.

For a biodegradable polymer having the antimicrobial function useful in the present invention, the molar ratio of the segment A and the segment B preferably is 1:0.007-1.2, more preferably 1:0.5-1.2.

The molecular weight of a biodegradable polymer having the antimicrobial function useful in the present invention is not particularly limited. In view of convenience in operation, the molecular weight is preferably 500-2,000,000, and more preferably 1,000-2,000,000.

The biodegradable polymer having the antimicrobial function disclosed in the present invention is totally soluble in water, and thus, if desired, an antimicrobial solution can be further prepared in an aqueous solution at any concentration based on the applications and requirements, which is not particularly limited herein. However, the concentration of the antimicrobial solution useful in the present invention preferably is not greater than 10 wt %, so as to avoid the case where the content of the antimicrobial polymer in the solution is too high, such that the polymer is reacted with water to release an irritating halogen gas.

The antimicrobial efficacy of the antimicrobial solution disclosed in the present invention is achieved by a segment B contained in the biodegradable polymer having the antimicrobial function, in which the segment B comprises an N-halamine group having the antimicrobial property. Particularly, the content of the segment B containing the N-halamine group in the antimicrobial solution preferably is not less than 2 mmol/L, more preferably not less than 4 mmol/L, and most preferably between 4-200 mmol/L.

In order to maintain a better antimicrobial effect of the antimicrobial solution of the present invention, the antimicrobial solution useful in the present invention preferably has a pH in the range of 6-8; this is because that in a basic environment of a too high pH, the oxidation degree of the halogenating agent is low and the reaction rate is slow and thus the effect is poor. On the contrary, when the pH is smaller than 6, the reaction rate is easily increased, resulting in the breakage of the amide bond and the decrease of the molecular weight, such that the structure of the biodegradable polymer of the present invention is destroyed.

In order to control and maintain the pH of the mixture solution above within the preferred range above during the reaction, a pH buffer agent can be selectively added to the mixture solution to adjust the pH thereof.

The pH buffer agent useful in the present invention is not particularly limited, including, but not limited to, aqueous phosphoric acid solution, aqueous ammonium chloride solution, aqueous acetic acid solution, aqueous sodium hydrogen phosphate solution, aqueous disodium hydrogen phosphate solution, aqueous benzoic acid solution, or a mixture thereof.

The antimicrobial efficacy of the biodegradable polymer having the antimicrobial function disclosed in the present invention is achieved by the N-halamine group above. The N-halamine group of N—X (X can be Cl, Br, or I) can slowly dissociate by the action of water molecule in water in the presence of microorganisms, to release oxidizing halogen ions, which can kill microorganisms such as bacteria and molds, and thus the antimicrobial efficacy can be obtained. When the halogen ion is released from the polymer, the original N-halamine group of N—X can be reduced to N—H. At this time, if only the biodegradable polymer of the present invention is treated with the halogenating agent again, for example, by soaking or spraying, after being oxidized with the halogenating agent, the biodegradable polymer of the present invention can obtain the N-halamine group of N—X thereon again, thereby achieving the regenerated antimicrobial function.

In the biodegradable polymer having the antimicrobial function disclosed in the present invention, the halogen ion will be released from the N-halamine group through dissociation and consumed in the sterilization process, while the N-halamine group will be reduced to the amine bond N—H. If the antimicrobial property is not further regenerated with the halogenating agent thereafter, then the biodegradable polymer of the present invention will become a known polypeptide compound. The peptide linkage of the polypeptide compound will be broken by the action of microorganisms and fungi, and finally degraded into $NH_3$, $CO_2$, and $H_2O$, which are harmless to the environment. Thus, the biodegradable polymer disclosed in the present invention is a biodegradable and environment-friendly compound.

Several examples are set forth below to describe the method of the present invention in more detail, which, however, are for illustrative purposes only and are not intended to limit the present invention, and the scope of the present invention is defined by the appended claims.

EXAMPLES

Determination of Content of N—Cl N-Halamine Group

The determination of the content of the N—Cl N-halamine group in the polymer was carried out by a titration method, comprising:

1. At first, 5 g sodium thiosulfate (Aldrich, US) was diluted with purified water to 200 ml, to prepare a sodium thiosulfate titrant.

2. 0.5 g of the polymer to be determined was weighted, and then 1 g KI powder (Aldrich, US) and 40 ml purified water were added and continuously stirred until the powder was totally dissolved. If necessary, a small amount of acetic acid could be added as catalyst.

3. The mixture in step 2 was titrated with the sodium thiosulfate titrant in step 1, using a starch reagent (Aldrich, US) as indicator. A titration end point is reached as the solution turns colorless and clear from reddish-brown. The volume of the sodium thiosulfate titrant used was recorded.

4. The reaction equation of the titration is shown in the formula (a) below:

$$NCl + 2I^- + H^+ \rightarrow Cl^- + NH + I_2$$

$$I_2 + 2S_2O_3^{2-} \rightarrow 2I^- + S_4O_6^{2-} \tag{a}$$

According to this reaction equation, the content of the N—Cl N-halamine group per g polymer and further the molar ratio of the segment B containing the N-halamine group and the segment A containing no N-halamine group, could be obtained by the moles of the sodium thiosulfate titrant used.

Preparation of Polyglutamic Acid Chlorides Having Various Molar Ratios of Segment B and Segment A Example 1

10.0 g polyglutamic acid (PGA-$Na^+$, Mw ~2,000,000, Vedan, Taiwan) was placed into a 250 ml one-necked flask, and 90 ml purified water was added to dissolve it, to prepare an aqueous polyglutamic acid solution. Then, 4 g of 12.65 wt % aqueous sodium hypochlorite solution was added to form a mixture. The mixture was continuously stirred for 30 min at room temperature, so that polyglutamic acid was reacted with sodium hypochlorite. The reacted mixture was placed in a separatory funnel to precipitate the polymer 1 with isopropanol, which was separated from the funnel and dried in a vacuum oven. The dried product was a white to yellowish powder, which was totally soluble when it was dissolved in water. The dried polymer 1 was titrated with sodium thiosulfate, and finally, the molar ratio of the segment B containing the N-halamine group and the segment A containing no N-halamine group was calculated.

Examples 2-6

The same procedures as described in example 1 were used, except that the aqueous sodium hypochlorite solution was added to the aqueous polyglutamic acid solution at a weight of 12, 20, 28, 36, and 40 g, respectively. The mixture was continuously stirred for 30 min at room temperature, so that polyglutamic acid was reacted with sodium hypochlorite. The reacted mixtures were placed in a separatory funnel respectively to precipitate the polymers 2-6 with isopropanol, which were separated from the funnel and dried in a vacuum oven. The dried products each were a white to yellowish powder, which were totally soluble when they were dissolved in water. The dried polymers 2-6 were titrated with sodium thiosulfate respectively, and finally, the molar ratios of the segment B containing the N-halamine group and the segment A containing no N-halamine group were calculated.

Examples 7-8

The same procedures and mixture ratio as described in example 1 were used, except that the stirring times of the mixtures at room temperature were prolonged to 90 and 180 min respectively. After the reaction time was reached, similarly, the reacted mixtures were placed in a separatory funnel respectively to precipitate the polymers 7-8 with isopropanol, which were separated from the funnel and dried in a vacuum oven. The dried products each were a white to yellowish powder, which were totally soluble when they were dissolved in water. The dried polymers 7-8 were titrated with sodium thiosulfate respectively, and finally, the molar ratios of the segment B containing the N-halamine group and the segment A containing no N-halamine group were calculated.

Example 9

The same procedures as described in example 1 were used, except that the aqueous sodium hypochlorite solution was added to the aqueous polyglutamic acid solution at a weight of 80 g. Moreover, the stirring time of the mixture at room temperature was prolonged to 1440 min. After the reaction time was reached, the reacted mixture was placed in a separatory funnel to precipitate the polymer 9 with isopropanol, which was separated from the funnel and dried in a vacuum oven. The dried product was a white to yellowish powder, which was totally soluble when it was dissolved in water. The dried polymer 9 was titrated with sodium thiosulfate, and finally, the molar ratio of the segment B containing the N-halamine group and the segment A containing no N-halamine group was calculated.

Example 10

5.0 g polyglutamic acid was placed into a 500 ml one-necked flask, and 167 ml purified water was added to dissolve it, to prepare an aqueous polyglutamic acid solution. Then, 54 g of 4.89 wt % aqueous sodium hypochlorite solution was added, and the pH was adjusted to 6-8 with 0.5 N aqueous phosphoric acid solution, to form a mixture. The mixture was continuously stirred for 1 min at room temperature, so that polyglutamic acid was reacted with sodium hypochlorite. The reacted mixture was placed in a separatory funnel to precipitate the polymer 10 with isopropanol, which was separated from the funnel and dried in a vacuum oven. The dried product was a white to yellowish powder, which was totally soluble when it was dissolved in water. The dried polymer 10 was titrated with sodium thiosulfate, and finally, the molar ratio of the segment B containing the N-halamine group and the segment A containing no N-halamine group was calculated.

Examples 11-12

The same procedures and mixture ratio as described in example 10 were used, except that the stirring time of the mixtures at room temperature were prolonged to 5 and 10 min respectively. After the reaction time was reached, similarly, the reacted mixtures were placed in a separatory funnel respectively to precipitate the polymers 11-12 with isopropanol, which were separated from the funnel and dried in a vacuum oven. The dried products each were a white to yellowish powder, which were totally soluble when they were dissolved in water. The dried polymers 11-12 were titrated with sodium thiosulfate respectively, and finally, the molar ratios of the segment B containing the N-halamine group and the segment A containing no N-halamine group were calculated.

Preparation of Polyaspartic Acid Chlorides Having Various Molar Ratios of Segment B and Segment A Example 13

10.0 g polyaspartic acid (PASP, Mw ~5000, Taihe Water Treatment, China) was placed into a 500 ml one-necked flask, and 80 ml purified water was added to dissolve it, to prepare an aqueous polyaspartic acid solution. Then, 94 g of 6.84 wt % aqueous sodium hypochlorite solution was added, and the pH was adjusted to 6-8 with 1 N aqueous hydrochloric acid solution, to form a mixture. The mixture was continuously stirred for 12 h at room temperature, so that polyaspartic acid was reacted with sodium hypochlorite. The reacted mixture was placed in a separatory funnel to precipitate the polymer 13 with ethanol, which was separated from the funnel and dried in a vacuum oven. The dried product was a white to yellowish powder, which was totally soluble when it was dissolved in water. The dried polymer 13 was titrated with sodium thiosulfate, and finally, the molar ratio of the segment B containing the N-halamine group and the segment A containing no N-halamine group was calculated.

Example 14

10.0 g polyaspartic acid was placed into a 500 ml one-necked flask, and 80 ml purified water was added to dissolve it, to prepare an aqueous polyaspartic acid solution. Then, 188 g of 6.84 wt % aqueous sodium hypochlorite solution was added, and the pH was adjusted to 6-8 with 1 N aqueous hydrochloric acid solution, to form a mixture. The mixture was continuously stirred for 12 h at room temperature, so that polyaspartic acid was reacted with sodium hypochlorite. The reacted mixture was placed in a separatory funnel to precipitate the polymer 14 with ethanol, which was separated from the funnel and dried in a vacuum oven. The dried product was a white to yellowish powder, which was totally soluble when it was dissolved in water. The dried polymer 14 was titrated with sodium thiosulfate, and finally, the molar ratio of the segment B containing the N-halamine group and the segment A containing no N-halamine group was calculated.

Example 15

10.0 g polyaspartic acid was placed into a 500 ml one-necked flask, and 50 ml purified water was added to dissolve it, to prepare an aqueous polyaspartic acid solution. Then, 70.2 g of 9.23 wt % aqueous sodium hypochlorite solution was added, and the pH was adjusted to 6-8 with 1 N aqueous hydrochloric acid solution, to form a mixture. The mixture was continuously stirred for 3 h at room temperature, so that polyaspartic acid was reacted with sodium hypochlorite. The reacted mixture was placed in a separatory funnel to precipitate the polymer 15 with ethanol, which was separated from the funnel and dried in a vacuum oven. The dried product was a white to yellowish powder, which was totally soluble when it was dissolved in water. The dried polymer 15 was titrated with sodium thiosulfate, and finally, the molar ratio of the segment B containing the N-halamine group and the segment A containing no N-halamine group was calculated.

Comparative Examples

Untreated polyglutamic acid and polyaspartic acid of each 10 g were respectively used as polymer C1 and polymer C2 as controls for comparison.

The mixture ratios, reaction time, and the molar ratios of the segment B containing the N-halamine group and the segment A containing no N-halamine group in the examples were summarized in tables 1 and 2 below.

TABLE 1

| Polymer No. | PGA (g) | Aqueous Sodium Hypochlorite Solution (g) | Sodium Hypochlorite (g) | Reaction Time (min) | Molar Ratio of Segment B to Segment A |
|---|---|---|---|---|---|
| C1 | 10 | 0 | 0 | 0 | 0 |
| 1 | 10 | 4 | 0.51 | 30 | 0.07 |
| 2 | 10 | 12 | 1.52 | 30 | 0.14 |
| 3 | 10 | 20 | 2.53 | 30 | 0.23 |
| 4 | 10 | 28 | 3.54 | 30 | 0.37 |
| 5 | 10 | 36 | 4.55 | 30 | 0.56 |
| 6 | 10 | 40 | 5.06 | 30 | 0.61 |
| 7 | 10 | 40 | 5.06 | 90 | 1.07 |
| 8 | 10 | 40 | 5.06 | 180 | 0.85 |
| 9 | 10 | 80 | 10.12 | 1440 | 0.33 |
| 10 | 5 | 54 | 2.64 | 1 | 0.02 |
| 11 | 5 | 54 | 2.64 | 5 | 0.03 |
| 12 | 5 | 54 | 2.64 | 10 | 0.06 |

TABLE 2

| Polymer No. | PASP (g) | Aqueous Sodium Hypochlorite Solution (g) | Sodium Hypochlorite (g) | Reaction Time (hour) | Molar Ratio of Segment B to Segment A |
|---|---|---|---|---|---|
| C2 | 10 | 0 | 0 | 0 | 0 |
| 13 | 10 | 94 | 6.43 | 12 | 0.03 |
| 14 | 10 | 188 | 12.86 | 12 | 0.02 |
| 15 | 10 | 70.2 | 6.48 | 3 | 0.007 |

Antimicrobial Test

The antimicrobial activity test of most of antimicrobial agents was evaluated for resistance to a wide range of microorganisms including Gram-positive and Gram-negative microorganisms. The test bacteria of the present invention were *Staphylococcus aureus* (BCRC Number 15211) and *Escherichia coli* (BCRC Number 11446). Here, the *Staphylococcus aureus* is a Gram-positive bacterium and the *Escherichia coli* is a Gram-negative bacterium.

A. Culture of Strains

A single colony of the *Staphylococcus aureus* and a single colony of the *Escherichia coli* were picked from a preserved agar medium, and inoculated to a 15 mL centrifugal tube containing 2000 µL LB broth respectively. Then, the centrifugal tube was shaken for 10 min and after the bacteria was well dispersed and suspended, the formed stock solution was subjected to 10-fold serial dilution with LB broth, to obtain diluted solutions having various dilution factors ($10^{-1}$, $10^{-2}$, $10^{-3}$, $10^{-4}$, and $10^{-5}$). Afterwards, 100 µL the solutions of *Staphylococcus aureus* and *Escherichia coli* having various dilution factors were inoculated onto different agar media and uniformly plated with a triangular glass rod, respectively. Then, the agar media plated with the solutions were placed into an incubator at 37° C. and grown for 14-24 h, and at this time, the growth in the solutions having various dilution factors after plating could be observed and the colony forming units in the agar range (20-300 CFU) could be counted, whereby it can be confirmed that the bacteria can normally grow in this environment. Then, based on the calculated colony forming units in the agar media, a suitable amount of the stock solution was adjusted with sterile water, to obtain a test solution of $10^6$-$10^7$ CFU/mL.

B. Qualitative Antimicrobial Test

The two test solutions above (*Staphylococcus aureus* and *Escherichia coli*) of each 100 µL were inoculated onto different agar media and uniformly plated with a triangular glass rod, respectively. Next, the polymers 1-15 and polymers C1 and C2 were respectively made into a tablet, and the tablets were horizontally adhered onto the agar media plated with the test solutions as described above, respectively. Then, the agar media were placed in an incubator at 37° C. and grown for 14-24 h, and at this time, the surface and surroundings of the tablets were observed. It could be clearly seen with the naked eye that, no colony was formed on the surface and surroundings of the tablets of the polymers 1-15, and there were colonies formed on those of the polymers C1 and C2.

C. Quantitative Antimicrobial Test

The evaluation in this test was carried out according to the antimicrobial standards of ASTM E2149 under dynamic contact conditions. In this test, the two test solutions above (*Staphylococcus aureus* and *Escherichia coli*) were diluted 10-fold to control the concentration to be $10^5$-$10^6$ CFU/mL, respectively, as test solutions in this test.

The polymers 1-15 of each 125 mg and the polymers C1 and C2 as controls of each 125 mg were weighted and inoculated with 5 mL of the test solutions and incubated. After 24 h of incubation, bacterial counts without incubation (P) and bacterial counts with incubation (Q) of the test examples above were determined respectively. After the resultant bacterial counts above were calculated, the antibacterial activity could be calculated by the following equation (b):

$$\text{Antibacterial activity} = \frac{P-Q}{P} \times 100\% \quad (b)$$

in which, P is bacterial counts with inoculation and without incubation; Q is bacterial counts with inoculation and with 24 h of incubation. When Q is much greater than P, it is indicative of no antimicrobial activity. The antimicrobial activities of the polymers 1-15 and control polymers C1 and C2 are shown in tables 3 and 4 below.

TABLE 3

Antimicrobial activity with *Staphylococcus aureus* as test solution (based on ASTM E2149 under dynamic contact conditions)

| Polymer No | Colony Density (CFU/cm²) 0 h | 24 h | Antimicrobial Activity (%) |
|---|---|---|---|
| C1 | 3.65 × 10⁵ | 7.97 × 10⁷ | 0 |
| C2 | 3.42 × 10⁵ | 6.53 × 10⁷ | 0 |
| 1 | 3.51 × 10⁵ | 0 | >99.9 |
| 2 | 2.98 × 10⁵ | 0 | >99.9 |
| 3 | 3.44 × 10⁵ | 0 | >99.9 |
| 4 | 2.89 × 10⁵ | 0 | >99.9 |
| 5 | 3.82 × 10⁵ | 0 | >99.9 |
| 6 | 3.36 × 10⁵ | 0 | >99.9 |
| 7 | 3.51 × 10⁵ | 0 | >99.9 |
| 8 | 3.73 × 10⁵ | 0 | >99.9 |
| 9 | 3.27 × 10⁵ | 0 | >99.9 |
| 10 | 2.95 × 10⁵ | 0 | >99.9 |
| 11 | 2.99 × 10⁵ | 0 | >99.9 |
| 12 | 3.01 × 10⁵ | 0 | >99.9 |
| 13 | 3.22 × 10⁵ | 0 | >99.9 |
| 14 | 3.53 × 10⁵ | 0 | >99.9 |
| 15 | 3.48 × 10⁵ | 0 | >99.9 |

TABLE 4

Antimicrobial activity with *Escherichia coli* as test solution (based on ASTM E2149 under dynamic contact conditions)

| Polymer No | Colony Density (CFU/cm²) 0 h | 24 h | Antimicrobial Activity (%) |
|---|---|---|---|
| C1 | 2.82 × 10⁵ | 6.50 × 10⁷ | 0 |
| C2 | 3.26 × 10⁵ | 7.02 × 10⁷ | 0 |
| 1 | 3.13 × 10⁵ | 0 | >99.9 |
| 2 | 3.44 × 10⁵ | 0 | >99.9 |
| 3 | 3.57 × 10⁵ | 0 | >99.9 |
| 4 | 3.46 × 10⁵ | 0 | >99.9 |
| 5 | 3.22 × 10⁵ | 0 | >99.9 |
| 6 | 3.61 × 10⁵ | 0 | >99.9 |
| 7 | 3.37 × 10⁵ | 0 | >99.9 |
| 8 | 3.76 × 10⁵ | 0 | >99.9 |
| 9 | 3.56 × 10⁵ | 0 | >99.9 |
| 10 | 3.45 × 10⁵ | 0 | >99.9 |
| 11 | 3.34 × 10⁵ | 0 | >99.9 |
| 12 | 3.59 × 10⁵ | 0 | >99.9 |
| 13 | 3.15 × 10⁵ | 0 | >99.9 |
| 14 | 3.26 × 10⁵ | 0 | >99.9 |
| 15 | 3.37 × 10⁵ | 0 | >99.9 |

D. Quantitative Antimicrobial Test

The evaluation in this test was carried out according to the antimicrobial standard of AATCC 100 under static contact conditions. The polymers 1-15 and polymers C1 and C2 were processed onto a cotton cloth by an impregnation and padding method, respectively, and they were cut into square specimens of 2×2 cm² in size, horizontally adhered onto the bottom of a 50 mL serum bottle, respectively and inoculated with 20 µL $10^6$-$10^7$ CFU/mL of the test solutions (*Staphylococcus aureus* and *Escherichia coli*). After the test solutions were contacted with these square specimens, the square specimens were immediately washed with 20 mL sterile water, and bacteria counts with inoculation and without incubation (P) were determined. Another set of square specimens inoculated with the test solutions were taken, and these square specimens were incubated for 24 h after they were contacted with the test solutions, and then bacteria counts with incubation (Q) were determined.

The antibacterial activity could be calculated according to the equation (b) above. The antimicrobial activities of the polymers 1-15 and control polymers C1 and C2 are shown in tables 5 and 6 below. In tables 5 and 6, the colony density (CFU/cm$^2$) refers to a value obtained by dividing the number of colonies counted in the range of 2×2 cm$^2$ by the area of this range.

TABLE 5

Antimicrobial activity with *Staphylococcus aureus* as test solution (based on AATCC 100 under static contact conditions)

| Polymer No | Colony Density (CFU/cm$^2$) | | Antimicrobial Activity (%) |
|---|---|---|---|
| | 0 h | 24 h | |
| C1 | 6.95 × 10$^5$ | 8.55 × 10$^7$ | 0 |
| C2 | 6.87 × 10$^5$ | 7.96 × 10$^7$ | 0 |
| 1 | 7.03 × 10$^5$ | 0 | >99.9 |
| 2 | 6.14 × 10$^5$ | 0 | >99.9 |
| 3 | 6.63 × 10$^5$ | 0 | >99.9 |
| 4 | 7.16 × 10$^5$ | 0 | >99.9 |
| 5 | 5.22 × 10$^5$ | 0 | >99.9 |
| 6 | 5.61 × 10$^5$ | 0 | >99.9 |
| 7 | 6.37 × 10$^5$ | 0 | >99.9 |
| 8 | 6.76 × 10$^5$ | 0 | >99.9 |
| 9 | 7.26 × 10$^5$ | 0 | >99.9 |
| 10 | 6.95 × 10$^5$ | 0 | >99.9 |
| 11 | 5.83 × 10$^5$ | 0 | >99.9 |
| 12 | 7.01 × 10$^5$ | 0 | >99.9 |
| 13 | 6.94 × 10$^5$ | 0 | >99.9 |
| 14 | 7.21 × 10$^5$ | 0 | >99.9 |
| 15 | 6.72 × 10$^5$ | 0 | >99.9 |

TABLE 6

Antimicrobial activity with *Escherichia coli* as test solution (based on AATCC 100 under static contact conditions)

| Polymer No | Colony Density (CFU/cm$^2$) | | Antimicrobial Activity (%) |
|---|---|---|---|
| | 0 h | 24 h | |
| C1 | 5.82 × 10$^5$ | 7.53 × 10$^7$ | 0 |
| C2 | 5.78 × 10$^5$ | 7.25 × 10$^7$ | 0 |
| 1 | 6.13 × 10$^5$ | 0 | >99.9 |
| 2 | 5.24 × 10$^5$ | 0 | >99.9 |
| 3 | 5.57 × 10$^5$ | 0 | >99.9 |
| 4 | 5.75 × 10$^5$ | 0 | >99.9 |
| 5 | 7.64 × 10$^5$ | 0 | >99.9 |
| 6 | 6.83 × 10$^5$ | 0 | >99.9 |
| 7 | 7.05 × 10$^5$ | 0 | >99.9 |
| 8 | 5.96 × 10$^5$ | 0 | >99.9 |
| 9 | 6.36 × 10$^5$ | 0 | >99.9 |
| 10 | 5.93 × 10$^5$ | 0 | >99.9 |
| 11 | 6.73 × 10$^5$ | 0 | >99.9 |
| 12 | 7.17 × 10$^5$ | 0 | >99.9 |
| 13 | 6.73 × 10$^5$ | 0 | >99.9 |
| 14 | 6.58 × 10$^5$ | 0 | >99.9 |
| 15 | 5.87 × 10$^5$ | 0 | >99.9 |

It can be known from tables 3, 4, 5, and 6 that, the biodegradable polymers 1-15 of the present invention are shown to have good antimicrobial activity for the Gram-positive and Gram-negative bacteria.

E. Quantitative Antimicrobial Test at Minimum Antimicrobial Concentration

The evaluation in this test was carried out according to the antimicrobial standard of ASTM E2149 under dynamic contact conditions. 0.1-10 wt % of aqueous test solutions were prepared from the polymer 5 (for details, see table 7), and the antimicrobial activities of the polymer and the control polymer C1 were determined, respectively. It can be known from table 7 that, when the polymer 5 is tested at 0.1 wt %, that is, 2 mmol/L of the segment B is contained in the aqueous polymer 5 solution, the antimicrobial activity is 95.2%; when the polymer 5 is tested at 0.2 wt %, that is, 4 mmol/L of the segment B is contained in the aqueous polymer 5 solution, the antimicrobial activity is greater than 99.9%. Also, when the polymer 5 is tested at 10 wt %, that is, 200 mmol/L of the segment B is contained in the aqueous polymer 5 solution, the antimicrobial activity also is greater than 99.9%.

TABLE 7

| | Colony Density (CFU) | | Antimicrobial Activity (%) |
|---|---|---|---|
| | 0 h | 24 h | |
| Polymer C1 | 2.76 × 10$^5$ | 7.97 × 10$^7$ | 0 |
| 0.1 wt % | 3.61 × 10$^5$ | 7.05 × 10$^5$ | 95.2 |
| 0.2 wt % | 2.78 × 10$^5$ | 0 | >99.9 |
| 0.3 wt % | 3.84 × 10$^5$ | 0 | >99.9 |
| 0.4 wt % | 4.11 × 10$^5$ | 0 | >99.9 |
| 0.5 wt % | 3.56 × 10$^5$ | 0 | >99.9 |
| 0.6 wt % | 3.78 × 10$^5$ | 0 | >99.9 |
| 0.7 wt % | 3.91 × 10$^5$ | 0 | >99.9 |
| 0.8 wt % | 2.97 × 10$^5$ | 0 | >99.9 |
| 0.9 wt % | 2.57 × 10$^5$ | 0 | >99.9 |
| 10 wt % | 3.02 × 10$^5$ | 0 | >99.9 |

It can be known from table 7 that, when the content of the segment B in the aqueous solution is 2 mmol/L, the bacterial growth can be suppressed. Thus, the antimicrobial solution according to the present invention has antimicrobial efficacy, only if the content of the segment B in the antimicrobial solution is not less than 2 mmol/L.

However, the descriptions above only are preferred examples of the present invention and are not intended to limit the scope of the present invention, and simple and equivalent changes or modifications, made by any person skilled in the art without departing the spirit and scope of the present invention, all fall within the scope of the present invention.

What is claimed is:

1. A water-soluble and biodegradable antimicrobial agent, comprising a polymer composed of a segment A and a segment B, wherein the segment A has the following formula I:

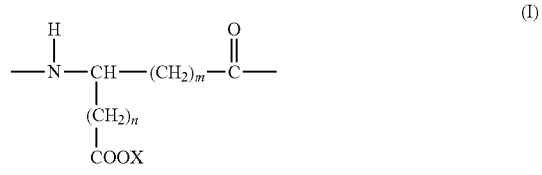

(I)

and the segment B has the following formula II:

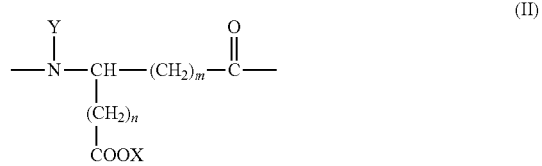

(II)

wherein the segment A and the segment B in the polymer have a molar ratio of 1:0.007-1.2, and n is 0 or 1, m is an integer of 0-2, m+n≠0, and X is H, Na, K, NH$_4$, ½Ca, or ½Mg, Y is Cl, Br, or I.

2. The antimicrobial agent of claim 1, wherein the segment A and the segment B in the polymer have a molar ratio of 1:0.5-1.2.

3. The antimicrobial agent of claim 1, wherein the segment A has the following formula:

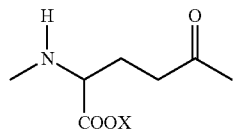

the segment B has the following formula:

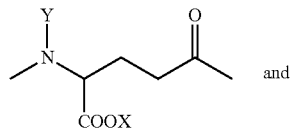 and wherein X is H, Na, K, NH$_4$, ½Ca, or ½Mg; and Y is Cl, Br, or I.

4. The antimicrobial agent of claim 1, wherein the segment A is selected from the group consisting of a segment C and a segment D, and the segment B is selected from the group consisting of a segment E and a segment F, wherein the segment C has the following formula:

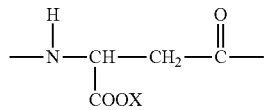

the segment D has the following formula:

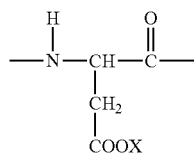

the segment E has the following formula:

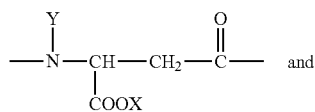 and the segment F has the following formula:

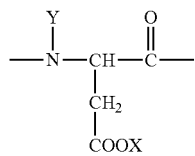

wherein X is H, Na, K, NH$_4$, ½Ca, or ½Mg, Y is Cl, Br, or I, and the ratio between the total moles of the segment C and the segment E and the total moles of the segment D and the segment F is not less than 1.

5. The antimicrobial agent of claim 1, wherein the polymer has a molecular weight of not greater than 2,000,000.

6. The antimicrobial agent of claim 1, wherein the polymer has a molecular weight of between 500 and 2,000,000.

7. The antimicrobial agent of claim 1, wherein the polymer has a molecular weight of between 1,000 and 2,000,000.

8. A biodegradable antimicrobial solution, comprising:
an aqueous solution; and
a biodegradable polymer having antimicrobial function, composed of a segment A and a segment B,
wherein the segment A has the following formula I:

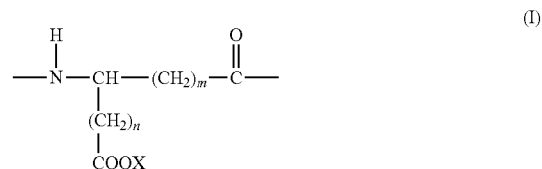 (I)

the segment B has the following formula II:

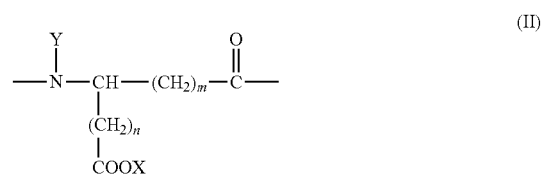 (II)

wherein n is 0 or 1, m is an integer of 0-2, m+n≠0, X is H, Na, K, NH$_4$, ½Ca, or ½Mg, Y is Cl, Br, or I, the molar ratio of the segment A and the segment B in the polymer is 1:0.007-1.2, and the content of the segment B in the antimicrobial solution is not less than 2 mmol/L.

9. The antimicrobial solution of claim 8, wherein the segment A and the segment B in the biodegradable polymer have a molar ratio of 1:0.5-1.2.

10. The antimicrobial solution of claim 8, wherein the content of the segment B in the antimicrobial solution is not less than 4 mmol/L.

11. The antimicrobial solution of claim 8, wherein the content of the segment B in the antimicrobial solution is 4-200 mmol/L.

12. The antimicrobial solution of claim 8, wherein the segment A has the following formula:

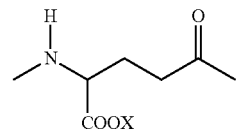

the segment B has the following formula:

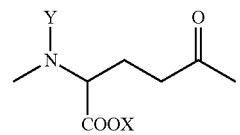

wherein X is H, Na, K, NH$_4$, ½Ca, or ½Mg; Y is Cl, Br, or I.

13. The antimicrobial solution of claim 8, wherein the segment A is selected from the group consisting of a segment C and a segment D, and the segment B is selected from the group consisting of a segment E and a segment F, wherein the segment C has the following formula:

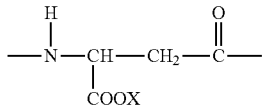

the segment D has the following formula:

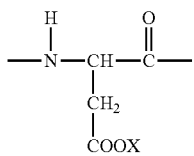

the segment E has the following formula:

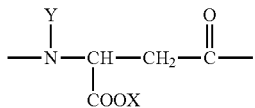

the segment F has the following formula:

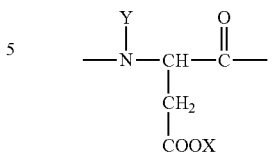

wherein X is H, Na, K, $NH_4$, ½Ca, or ½Mg, Y is Cl, Br, or I, and the ratio between the total moles of the segment C and the segment E and the total moles of the segment D and the segment F is not less than 1.

14. The antimicrobial solution of claim 8, wherein the biodegradable polymer has a molecular weight of not greater than 2,000,000.

15. The antimicrobial solution of claim 8, wherein the biodegradable polymer has a molecular weight of between 500 and 2,000,000.

16. The antimicrobial solution of claim 8, wherein the biodegradable polymer has a molecular weight of between 1,000 and 2,000,000.

17. The antimicrobial solution of claim 8, wherein the antimicrobial solution has a pH of 6-8.

18. The antimicrobial solution of claim 17, further comprising a pH buffer agent.

19. The antimicrobial solution of claim 18, wherein the pH buffer agent is an aqueous phosphoric acid solution, aqueous ammonium chloride solution, aqueous acetic acid solution, aqueous sodium hydrogen phosphate solution, aqueous disodium hydrogen phosphate solution, aqueous benzoic acid solution, or a mixture thereof.

20. The antimicrobial solution of claim 8, wherein the aqueous solution is water.

* * * * *